US008084018B2

(12) United States Patent
Hurtt

(10) Patent No.: US 8,084,018 B2
(45) Date of Patent: Dec. 27, 2011

(54) METHODS FOR IMAGING DOPAMINE TRANSPORTER LEVEL

(75) Inventor: Mark Hurtt, Wallingford, CT (US)

(73) Assignee: Alseres Pharmaceuticals, Inc., Hopkinton, MA (US)

( * ) Notice: Subject to any disclaimer, the term of this patent is extended or adjusted under 35 U.S.C. 154(b) by 958 days.

(21) Appl. No.: 11/931,979

(22) Filed: Oct. 31, 2007

(65) Prior Publication Data

US 2009/0110635 A1    Apr. 30, 2009

(51) Int. Cl.
*A61K 49/04* (2006.01)
(52) U.S. Cl. .............. 424/9.45; 424/1.11; 424/1.65; 424/1.81; 424/1.85; 424/1.89; 424/9.1; 424/9.4; 424/9.44
(58) Field of Classification Search ........... 424/1.11, 424/1.49, 1.65, 1.69, 1.73, 1.81, 1.85, 1.89, 424/9.1, 9.4, 9.42, 9.43, 9.44, 9.45, 9.451
See application file for complete search history.

(56) References Cited

U.S. PATENT DOCUMENTS

| 5,493,026 | A | 2/1996 | Elmaleh et al. | 346/132 |
|---|---|---|---|---|
| 5,506,359 | A | 4/1996 | Madras et al. | 546/130 |
| 5,770,180 | A | 6/1998 | Madras et al. | 424/1.81 |
| 5,853,696 | A | 12/1998 | Elmaleh et al. | 424/1.85 |
| 5,948,933 | A | 9/1999 | Meltzer et al. | 558/426 |
| 6,171,576 | B1 | 1/2001 | Meltzer et al. | 424/1.65 |
| 6,548,041 | B1 | 4/2003 | Meltzer et al. | 424/1.65 |
| 7,081,238 | B2 * | 7/2006 | Madras et al. | 424/1.65 |
| 2002/0150535 | A1 * | 10/2002 | Madras et al. | 424/1.65 |
| 2006/0257316 | A1 * | 11/2006 | Madras et al. | 424/1.11 |
| 2010/0143248 | A1 * | 6/2010 | Madras et al. | 424/1.65 |

OTHER PUBLICATIONS

Seibyl J, et al., Iodine-123-β-CIT and Iodine-123-FPCIT SPECT Measurement of Dopamine Transporters in Healthy Subjects and Parkinson's Patients, *J. Nucl. Med.* 39;1500-08, 1998.
Marek K. et al., A molecular map for neurodegeneration, *Science* 289: 409-11, 2000.
Seibyl J. et al., Decreased SPECT [$^{123}$-I]β-CIT striatal uptake correlates with symptom severity in Parkinson's disease, *American Neurological Association*, 38:589-98, 1995.
Seibyl J. et al., Test/retest reproducibility of Iodine-I23-βCIT SPECT brain measurement of dopamine transporters in Parkinson's patients, *J. Nucl. Med.* 38:1453-59, 1997.
Laruelle M. et al., Graphical, kinetic, and equilibrium analyses of in vivo [$^{123}$I]β-CIT binding to dopamine transporters in healthy human subjects., *J. Cereb. Blood Flow Metab.* 14:982-94, 1994.
Kugaya, A., et al., Changes in human in vivo serotonin and dopamine transporter availabilities during chronic antidepressant administration, *Neuropsychopharmacology*, 28(2).413-20, 2003.
Sahani, D., et al., Quantitative measurements of medical images for pharmaceutical clinical trials: comparison between on-site and off-site assessments, *AJR Am J Roentgenol*. 2000. 174(4): 1159-62.
Fischman, A.J., et al., Rapid detection of Parkinson's disease by SPECT with altropane: a selective ligand for dopamine transporters, *Synapse*, 1998, 29(2): 128-41.
Madras, B.K., et al., Altropane, a SPECT or PET imaging probe for dopamine neurons: III. Human dopamine transporter in postmortem normal and Parkinson's diseased brain, *Synapse*, 1998. 29(2):116-27.
Madras, B.K., et al., Altropane, a SPECT or PET imaging probe for dopamine neurons: II. Distribution to dopamine-rich regions of primate brain, *Synapse*, 1998, 29(2):105-15.
Madras, B.K., et al., Altropane, a SPECT or PET imaging probe for dopamine neurons: I. Dopamine transporter binding in primate brain, *Synapse*, 1998. 29(2):93-104.
Fischman, A.J., et al., SPECT imaging of dopamine transporter sites in normal and MPTP-Treated rhesus monkeys, *J Nucl Med*, 38(1):144-50.
Madras, B.K., et al., Technepine: A high-affinity $^{99m}$Technetium probe to label the dopamine transporter in brain by SPECT imaging, *Synapse*, 1996. 22:239-46.
Farde, L, et al., Kinetic analysis of central [$^{11}$C] raclopride binding to $D_2$-Dopamine receptors studied by PET—a comparison to the equilibrium analysis, *J. Cereb. Blood Flow Metab.*, 1989, 9:696-08.
Meltzer, P.C., et al., Substituted 3-phenyltropane analogs of cocaine: synthesis, inhibition on binging at cocaine recognition sites, and positron emission tomography imaging, 1993, *J. Med, Chem,*, 36:855-62.
Milius, R.A., et al., Synthesis and receptor binding of N-substituted tropane derivative. High-affinity ligands for the cocaine receptor, 1991, *J. Med. Chem.*, 34, 1728-31.

* cited by examiner

*Primary Examiner* — D L Jones
(74) *Attorney, Agent, or Firm* — Rissman Hendricks & Oliverio LLP

(57) ABSTRACT

Presented is a method for assessing dopamine transporter levels in a selected area of a subject's central nervous system by SPECT imaging comprising administering an injection of a labeled dopamine transporter ligand at approximately the time the subject is positioned for SPECT imaging and initiating a SPECT acquisition for a duration of about 30 minutes commencing at about 15 minutes after administration of labeled dopamine transporter ligand; and assessing, based on said SPECT acquisition, the amount of labeled dopamine transporter ligand that is bound to dopamine transporter.

12 Claims, 4 Drawing Sheets

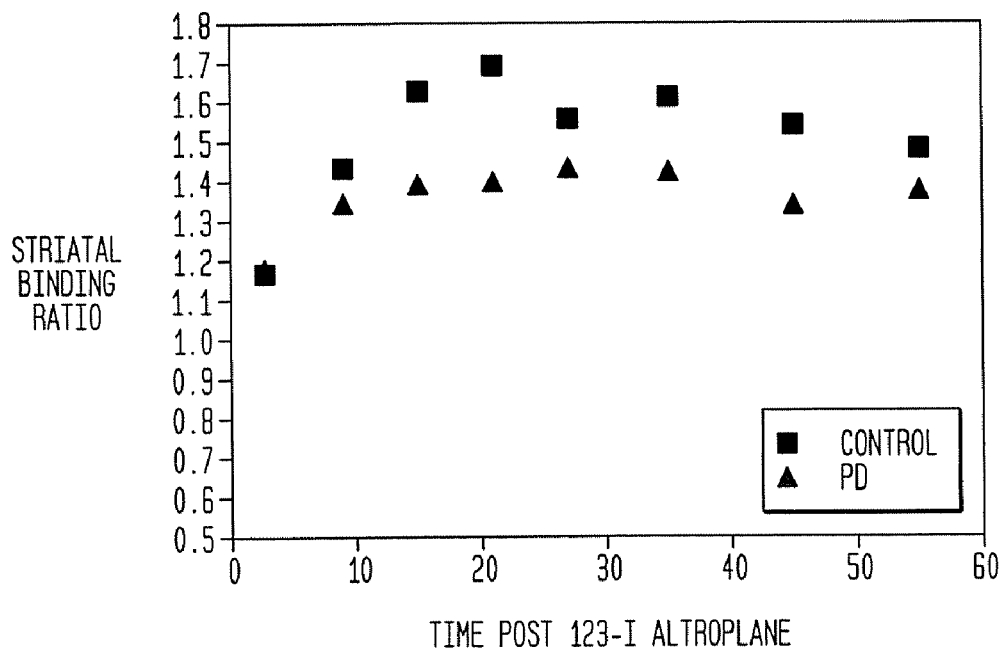
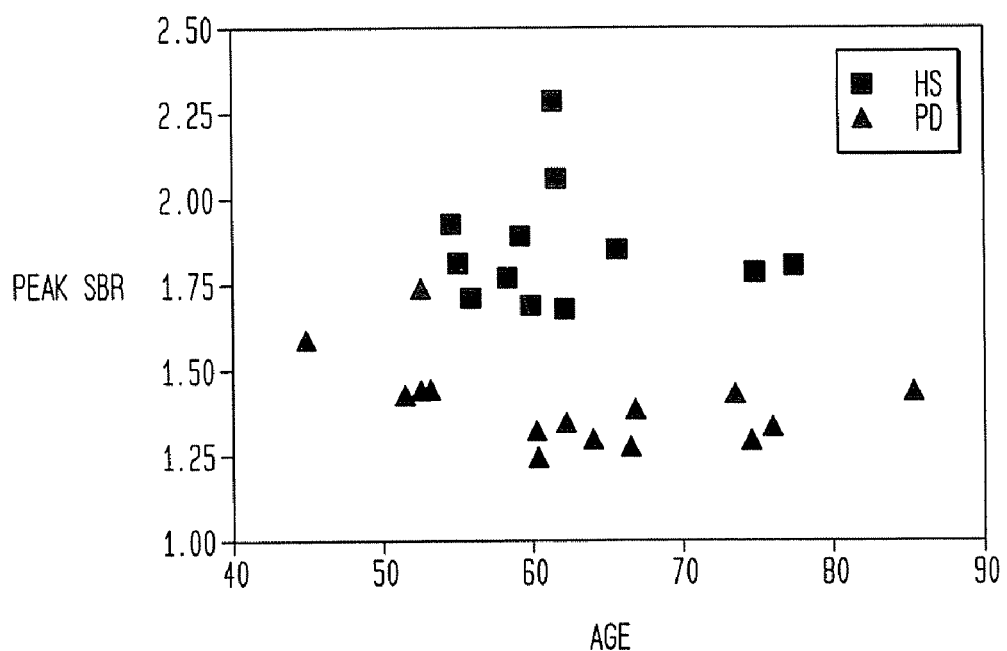

METHODS FOR IMAGING DOPAMINE TRANSPORTER LEVEL

FIELD OF THE INVENTION

The present invention relates to imaging the dopamine transporter, and to diagnosing and monitoring neurological disorders.

BACKGROUND OF THE INVENTION

There is a need for improved diagnostic methods for neurological disorders. There is a particular need for methods for diagnosing neurological disorders that selectively target a dopamine transporting protein (the dopamine transporter) and can distinguish it from another protein known as the serotonin transporter. In normal brain tissue, the dopamine:serotonin transporter density ratio is approximately 10:1. In certain neurodegenerative disorders, such as Parkinson's disease, nerve cells that produce dopamine (and on which the dopamine transporter is located) undergo severe depletion, while serotonin nerve cells are less affected. The dopamine:serotonin transporter ratio can fall to 2:1 in Parkinson's disease.

Another neurodegenerative disorder is Lewy Body Dementia, also referred to as Dementia with Lewy Bodies (DLB). DLB, after Alzheimer's disease, is the second most frequent cause of degenerative dementia in elderly adults. DLB is characterized by both loss of dopamine-producing neurons in the substantia nigra, similar to the loss seen in Parkinson's disease, and loss of acetylcholine-producing neurons in the basal nucleus of Meynert and elsewhere. This aspect is similar to that seen in Alzheimer's disease.

SUMMARY OF THE INVENTION

The present invention provides methods for assessing dopamine transporter levels in the central nervous system of a subject.

In one aspect of the present invention, the method for assessing dopamine transporter levels in the central nervous system of a subject comprises: a) positioning a subject on an imaging table; b) administering to the subject, an injection of a labeled dopamine transporter ligand after the subject is positioned on the imaging table; c) initiating a single SPECT acquisition for a duration of about 30 minutes commencing at about 15 minutes after administration of the labeled dopamine transporter ligand; and d) assessing as to the subject the amount of labeled dopamine transporter ligand that is bound to dopamine transporter in at least one region of the subject's central nervous system. Injection of labeled dopamine transporter ligand by bolus or rapid infusion are noted as useful options.

In another aspect, the present invention provides a method of diagnosing or monitoring a neurological disorder in a subject comprising assessing dopamine transporter levels in the central nervous system of the subject. In one embodiment, the neurological disorder is dementia with Lewy bodies. In another embodiment, the neurological disorder is Parkinson's disease.

BRIEF DESCRIPTION OF THE DRAWINGS

FIG. 3 is a graphic presentation of dynamic striatal binding ratios for a PD and control subject following bolus injection of $^{123}$I Altropane.

FIG. 4 is a graphic presentation of peak striatal binding ratios (SBR) for PD and control subjects versus age.

DETAILED DESCRIPTION OF THE INVENTION

Figure 1:
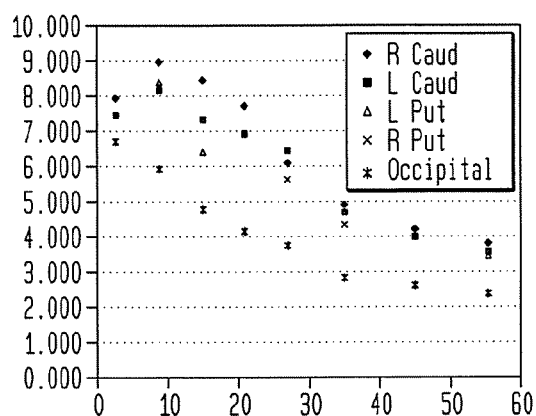
FIG. 1 is a graphic presentation of dynamic time-activity data for a healthy control subject receiving a bolus injection of $^{123}$I Altropane and imaged over 60 min.

In one aspect of the present invention, the method for assessing dopamine transporter levels in the central nervous system such as the brain and particularly the striatum of a subject comprises: a) Position a subject on an imaging table; b) administering to the subject an injection of a labeled dopamine transporter ligand (optionally $^{123}$I Altropane) after the subject is positioned on the imaging table; c) initiating a single SPECT acquisition for a duration of about 30 minutes, commencing at about 15 minutes after administration of the labeled dopamine transporter ligand; and d) assessing the amount of labeled dopamine transporter ligand that is bound to dopamine transporter in at least one region of the subject's central nervous system.

SPECT images may be acquired using a SPECT tomograph comprising one or more heads. In one embodiment, the SPECT acquisition is performed on a single headed SPECT tomograph. In another embodiment, the SPECT acquisition is performed on a dual headed SPECT tomograph. In another embodiment, the SPECT acquisition is performed on a triple headed SPECT tomograph.

In one embodiment, the labeled dopamine transporter ligand is administered at a dose ranging from about 1 mCi to about 10 mCi. In another embodiment, the labeled dopamine transporter ligand is administered at a dose ranging from about 5 mCi to about 8 mCi. In another embodiment, the labeled dopamine transporter ligand is administered at a dose of 8 mCi.

In another aspect, the present invention provides a method of diagnosing or monitoring a neurological disorder in a subject comprising assessing dopamine transporter levels in the central nervous system of the subject. In one embodiment, the neurological disorder is dementia with Lewy bodies. In another embodiment, the neurological disorder is Parkinson's disease.

As used herein, the term "dopamine transporter ligand" means a compound that binds to the dopamine transporter. In one embodiment, compounds bind selectively to the dopamine transporter in preference to the serotonin transporter.

The term "subject" means a patient in need of a treatment wherein treatment is broadly understood to include therapeutic, diagnostic, and prophylactic steps and procedures. In one embodiment, a subject is a mammal and particularly a human.

The term "selected area" means a central nervous system such as the brain and particularly the striatum of the brain of a subject.

In one aspect, the labeled dopamine transporter ligand is administered to the subject at approximately the time the subject is positioned for SPECT imaging. The term "approximately the time" refers to from about 60 minutes, and particularly about 30 minutes, more particularly about 15 minutes, to substantially immediately before or after a subject is positioned for SPECT imaging. In one embodiment, the subject is first positioned on an imaging table and then subsequently administered the dopamine transporter ligand. In another embodiment, the subject is first administered the dopamine transporter ligand and subsequently positioned on an imaging table.

As to scan times, it has been discovered that the signal-to-noise (S/N) ratio of the SPECT scans of the dopamine transporter ligand is optimal between the time of about 15 minutes and about 45 minutes post-injection of the dopamine transporter ligand.

Several alternatives are available for acquiring images. In one embodiment, the SPECT scanning is one continuous scan or a series of shorter scans. In another embodiment, the SPECT scanning comprises a series of one or more two minute scans. In another embodiment, the SPECT scanning comprises a series of one or more ten minute scans. In one particular embodiment, the SPECT images are generated using one continuous 30 minute scan. In another particular embodiment, the SPECT images are generated using a series of two minute scans for a period of 60 minutes. In another particular embodiment, the SPECT images are generated using a series of 4 minute scans for a period of 40 minutes.

Assessment of dopamine transporter levels, as in the course of a diagnostic investigation, can be performed by measuring dopamine transporter availability. Measurements can be made using devices such as positron emission tomography ("PET") or single photon emission computed tomography ("SPECT"). To measure dopamine transporter availability, a labeled probe that targets the transporter is introduced into the brain (e.g., intravenously) and PET or SPECT is performed. From the PET or SPECT data and images, the density of the dopamine transporter is quantified. In one embodiment, quantification is determined by computing binding potential, where binding potential is defined as the maximum number of binding sites, $B_{max}$, divided by a dissociation constant, $K_d$. The binding potential is calculated from a continuous scan starting at about 15 min. The region of interest is identified and the counts in that region are determined. Using appropriate modeling, numerical values for binding potential can be calculated and these values can be compared between subjects who have undergone equivalent treatment and scanning protocols. The striatal binding potential of $^{123}$I-Altropane (k3/k4) is calculated by the reference region approach as described by Farde, et al. (Farde, et al., 1989, *J. Cereb. Blood Flow Metab* 9:696 708).

Imaging agents that target the dopamine transporter include ($^{11}$C) Altropane, ($^{11}$C or $^{18}$F) WIN 35,428 (($^{11}$C) CFT), $^{123}$I Altropane, ($^{99m}$Tc) 0-1505, $^{99m}$Tc-technepine, and similar compounds. Without being bound by any particular theory, it is believed that these agents bind the dopamine transporter with varying affinities, allowing multiple, dissimilar assessments to be performed. Structures, synthesis, and/or sources of some of the above agents are described in Fischman et al., 1998, *Synapse* 29:125 41 (($^{123}$I) Altropane); Madras et al., 1996, *Synapse* 22:239 46; Meltzer et al., 1993, *J. Med. Chem.* 36:855 62; and Milius et al., 1990, *J. Medicinal Chem.* 34:1728 31, each of which is incorporated herein by reference in their entirety as are all references cited herein. Another useful compound includes $^{123}$I-Ioflupane (DatSCAN™, (Nycomed-Amersham, Piscataway, N.J.).

Examples of suitable ligands include ($^{11}$C)CFT (($^{11}$C)WIN 35,428), ($^{123}$I)Altropane®, and ($^{18}$F)CFT. Ligands particularly suitable for use in PET include, but are not limited to, ($^{11}$C) Altropane. Ligands suitable for use in SPECT include, but are not limited to, technetium-labeled phenyltropane probes, such as ($^{99m}$Tc) technepine, O-1505, and similar compounds. Other examples of compounds useful in the methods of the present invention are described in U.S. Pat. Nos. 5,493,026, 5,506,359, 5,770,180, 5,853,696, 5,948,933, 6,171,576, 6,548,041 and 7,081,238, the disclosures of which are hereby incorporated by reference. The portion of the subject's central nervous system for assessment is preferably a portion of the human brain, e.g., the striatum.

In one aspect, the invention employs $^{123}$I compounds as disclosed in U.S. Pat. No. 5,493,026, with particular reference to 2β-carbomethoxy-3β-(4'-flurophenyl)-N-(3-iodo-E-allyl) nortropane (ALTROPANE®, Alseres Pharmaceuticals, Inc. Hopkinton, Mass.) to differentiate neurological disorders. For these same functions, this invention also employs tropanes incorporating technetium (99 mTc) as a radiolabel as disclosed in U.S. Pat. Nos. 6,171,576 and 6,548,041.

The compounds described in U.S. Pat. No. 6,548,041 have a tropane compound linked through the nitrogen atom at the 8-position to a chelating ligand capable of complexing a technetium or rhenium radionuclide to produce a neutral labeled complex that selectively binds to the dopamine transporter. The tropane compounds is believed to bind to the dopamine transporter.

EXAMPLES

The following examples serve to illustrate certain useful embodiments and aspects of the present invention and are not to be construed as limiting the scope thereof. Alternative materials and methods can be utilized to obtain similar results.

Example 1

ALTROPANE® SPECT Imaging in Parkinson Disease and Control Subjects

The following example summarizes single photon emission computed tomographic (SPECT) image acquisition, analysis methods and results for Parkinson's disease research participants and healthy controls participating in an $^{123}$I Altropane SPECT imaging study. The experiment is an open label study evaluating time-activity curves and striatal dopamine transporter occupancy over the first hour post injection of $^{123}$I Altropane using temporally well-resolved dynamic SPECT in Parkinson's subjects and similarly aged healthy control subjects. In addition, for the PD subjects, a second injection and scan is performed on each subject on a separate test days to evaluate the test/retest reproducibility data for both visual and quantitative analyses.

A. Subjects and Drug Dosing

Fifteen idiopathic Parkinson's disease subjects are recruited through local advertising and word-of-mouth for enrollment in the study. Imaging is performed at Molecular NeuroImaging, LLC in New Haven, Conn., USA. $^{123}$I Altropane is studied under the auspices of a physician-sponsored IND # 76,024, Dr. J. Seibyl physician sponsor using test article provided by MDS Nordion, Inc (Vancouver, BC, Canada). All subjects are provided informed consent prior to any study procedures. All fifteen subjects completed two separate injection and SPECT scan sessions with approximately 296 mBq (8 mCi) of $^{123}$I Altropane. Subjects undergo motor ratings using the Unified Parkinson's Disease Rating Scale (UPDRS) following overnight period without anti-Parkinson medication administered by a movement disorder specialist. No PD subjects are terminated prior to achieving the study endpoint.

Twelve healthy control subjects are recruited for participation in a single scan session with $^{123}$I Altropane using the identical SPECT image acquisition protocol as the PD subjects. Healthy subjects are evaluated by a movement disorder specialist to confirm the absence of neurologic illness.

B. SPECT Imaging and Analysis

SPECT scans are acquired for 60 minutes following the intravenous injection with 296 mBq (8.0 mCi) of $^{123}$I Altropane. A series of dynamic SPECT scans are obtained as five scans at 6 minutes per acquisition followed by three scans at 10 minutes per acquisition. The subject remain in the camera for the duration of the acquisition. Each SPECT study is acquired on a Philips PRISM 3000XP triple-headed SPECT camera (Cleveland, Ohio, USA) fitted with fan-beam collimators. Each head rotates 360 degrees, sampling every 3 degrees for a total of 120 raw projection images per head. Projection data were collected in a 128×128 matrix within a symmetric energy window centered at 159 kEv (+/−10%). This acquisition protocol permits the post hoc analysis of imaging data at each time point using information from 1, 2, or all 3 heads, hence modeling the impact of different injected doses of $^{123}$I Altropane at 2.7, 5.3, and 8.0 mCi, respectively.

Data are re-constructed using filtered back projection and a simple ramp filter followed by a post hoc (3-D) standardized low pass filter. Attenuation correction was performed applying a Chang 0 correction and a mu of 0.11 cm$^{-1}$ using a standard or custom automated software package. Regions of interest (ROIs) are placed in the 3-head data with individual ROI sampling of the left and right caudate and putamen and an occipital background region. The ROIs were then applied to all images in the injection session (total of 24=8 time points×3 head conditions (1, 1&2, 1&2&3). To check for head movement within each scan session, five external skin fiducial markers containing 1 μCi of $^{123}$I were place along the canthomeatal line (2 right side, 3 left side) prior to each SPECT scan. Total counts within the ROI, total volume, and count density (counts/voxel) were extracted from each scan and logged in a data spreadsheet for determination of striatal uptake ratios (SBR) defined as the density of counts (counts per voxel per minute) in the striatal region divided by the density of counts in the occipital background region. The mean striatal SBR scores were calculated as the mean of the left and right caudate and putamen SBR scores. Since sampling in striatal subregions used the identical size ROI, there was equal contribution from left and right caudate and putamen to the mean SBR.

The time-activity data for mean striatal count densities and occipital background for each of the 8 images acquired in the 60 minutes post injection sampling period were plotted to permit visual interrogation of the uptake and washout characteristics of $^{123}$I Altropane in PD subjects and control subjects. In addition, each SBR ratio obtained at the 8 time points after injection were plotted. The peak SBR was assessed for each subject for data acquired using 1, 2, and 3 heads of imaging data.

For each PD subject a composite SBR ratio was determined for the scans (which are summed in FIG. 6) of each injection, corresponding to data collected over 13-40 minutes post injection (27 minutes total time). These time points were selected based on review of the peak and persistence of SBRs over the 60 minutes of image acquisition and a visual interrogation of the scan for optimal identification of striatal structures. This composite SBR was then compared within each subject's first and second $^{123}$I Altropane injection days to review the reproducibility of the SBR using the following equation:

(composite SBR first injection−composite SBR second injection)/(composite SBR first injection).

FIG. 3. is a plot of dynamic striatal binding ratios for a PD and control subject following bolus injection of $^{123}$I Altropane. Note that there is relative stability of the binding ratios by about 15 minutes post injection. This suggests that commencing image acquisitions 15 minutes after $^{123}$I Altropane injection will provide optimal signal:noise information.

FIG. 4. is a plot of peak striatal binding ratios (SBR) for PD and control subjects versus age. The SBR is determined as the single scan post injection demonstrating highest uptake. While this outcome measure is not an accurate quantitative measure for assessing dopamine transporter density, it nonetheless provides excellent separation between this group of well-characterized PD subjects and healthy controls.

C. Results

All 15 PD subjects enrolled completed the trial with a baseline and retest $^{123}$I Altropane SPECT studies and all 12 healthy controls completed all imaging assessments for a single study with $^{123}$I Altropane. All imaging data was of good technical quality with adequate counting statistics in the raw projection data sets and included in the analysis. No scans needed to be eliminated for technical reasons (e.g. head movement, low injected dose, or other reason for sub-optimal quality). Subject demographic are summarized in Table 1.

TABLE 1

Parkinson subjects: Demographics and UPDRS motor ratings

| PD Subject No. | Gender | Age | Duration DX | Altropane Dose (mCi) | HY | Total UPDRS | Motor UPDRS |
|---|---|---|---|---|---|---|---|
| 1 | Male | 67.0 | 1.0 | 8.6 | 2 | 35 | 27 |
| 2 | | | | 6.6 | 2 | 35 | 27 |
| 3 | Male | 66.0 | 10.0 | 6.6 | 2 | 48 | 28 |
| 4 | | | | 8.2 | 2 | 46 | 26 |
| 5 | Male | 51.6 | 6.1 | 8.1 | 2 | 23 | 16 |
| 6 | | | | 8.5 | 2 | 23 | 16 |
| 7 | Male | 64.0 | 10.0 | 6.8 | 1 | 22 | 9 |
| 8 | | | | 8.5 | 2 | 30 | 17 |
| 9 | Male | 74.6 | 9.2 | 8.4 | 2 | 31 | 21 |
| 10 | | | | 8.2 | 2 | 38 | 24 |
| 11 | Female | 60.6 | 7.8 | 8.2 | 3 | 46 | 27 |
| 12 | | | | 8.3 | 3 | 40 | 26 |
| 13 | Male | 73.5 | 3.0 | 8.4 | 1 | 20 | 17 |
| 14 | | | | 8.6 | 1 | 15 | 12 |
| 15 | Male | 52.7 | 2.0 | 8.2 | 2 | 45 | 31 |
| 16 | | | | 8.4 | 2 | 46 | 31 |
| 17 | Female | 52.7 | 1.0 | 8.4 | 2 | 27 | 20 |
| 18 | | | | 8.4 | 2 | 28 | 20 |
| 19 | Male | 44.9 | 10.6 | 8.4 | 2 | 46 | 34 |
| 20 | | | | 8.4 | 2 | 35 | 23 |
| 21 | Male | 60.4 | 6.9 | 8.3 | 2 | 31 | 18 |
| 22 | | | | 8.4 | 2 | 36 | 21 |
| 23 | Female | 85.4 | 2.2 | 8.4 | 1 | 13 | 6 |
| 24 | | | | 8.1 | 1 | 13 | 6 |
| 25 | Male | 76.0 | 4.3 | 8.2 | 2 | 27 | 17 |
| 26 | | | | 8.7 | 2 | 23 | 15 |
| 27 | Female | 53.2 | 8.7 | 6.7 | 2 | 42 | 25 |
| 28 | | | | 8.4 | 2 | 44 | 26 |
| 29 | Male | 62.3 | 13.0 | 8.5 | 2 | 30 | 20 |
| 30 | | | | 8.7 | 2 | 30 | 19 |

Note that each subject has paired scans consecutively numbered, e.g., Scans 1 and 2 are the same patient.

TABLE 2

Healthy control subjects

| Control Subject No. | Gender | Age | Altropane Dose (mCi) |
|---|---|---|---|
| 1 | Male | 62.3 | 7.92 |
| 2 | Female | 65.8 | 8.64 |
| 3 | Male | 58.4 | 8.57 |
| 4 | Male | 77.2 | 8.3 |
| 5 | Female | 74.9 | 8.5 |
| 6 | Male | 61.7 | 8.47 |
| 7 | Male | 60.1 | 8.46 |
| 8 | Male | 55.3 | 8.08 |
| 9 | Female | 59.3 | 8.75 |
| 10 | Female | 54.7 | 8.62 |
| 11 | Male | 61.2 | 8.42 |
| 12 | Male | 55.9 | 8.37 |

TABLE 3

Peak Striatal:Occipital Ratios

| PD | 3 head | 2 head | 1 head | Controls | 3 head | 2 head | 1 head |
|---|---|---|---|---|---|---|---|
| 1 | 1.39 | 1.37 | 1.33 | 1 | 1.68 | 1.55 | 1.50 |
| 2 | 1.28 | 1.27 | 1.41 | 2 | 1.86 | 1.84 | 1.66 |
| 3 | 1.43 | 1.39 | 1.33 | 3 | 1.77 | 1.61 | 1.51 |
| 4 | 1.30 | 1.28 | 1.29 | 4 | 1.81 | 1.66 | 1.49 |
| 5 | 1.30 | 1.27 | 1.24 | 5 | 1.79 | 1.67 | 1.57 |
| 6 | 1.25 | 1.25 | 1.22 | 6 | 2.06 | 1.95 | 1.79 |
| 7 | 1.44 | 1.41 | 1.35 | 7 | 1.69 | 1.62 | 1.47 |
| 8 | 1.44 | 1.46 | 1.41 | 8 | 1.81 | 1.68 | 1.56 |
| 9 | 1.74 | 1.66 | 1.52 | 9 | 1.90 | 1.79 | 1.63 |
| 10 | 1.60 | 1.53 | 1.43 | 10 | 1.93 | 1.77 | 1.64 |
| 11 | 1.33 | 1.26 | 1.26 | 11 | 2.30 | 2.10 | 1.86 |
| 12 | 1.34 | 1.28 | 1.24 | 12 | 1.71 | 1.59 | 1.52 |
| 13 | 1.45 | 1.36 | 1.29 | | | | |
| 14 | 1.35 | 1.32 | 1.26 | | | | |
| 15 | 1.45 | 1.43 | 1.32 | | | | |
| mean SBR | 1.41 | 1.37 | 1.33 | mean SBR | 1.86 | 1.74 | 1.60 |
| % COV | 9.1 | 8.5 | 6.5 | % COV | 9.4 | 9.4 | 7.6 |

Dynamic Time Activity Data for $^{123}$I Altropane in PD

Figure 1A:
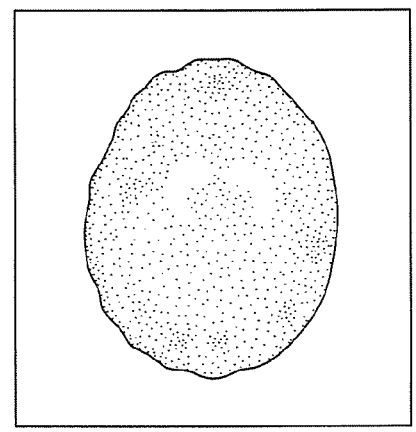
FIG. 1a is an image showing characteristic striatal uptake and homogeneous cortical background.
Figure 2:
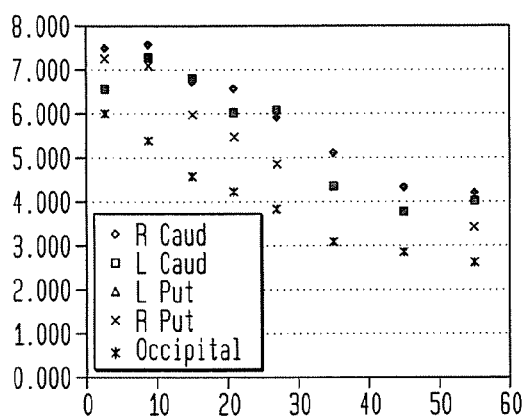
FIG. 2 is a graphic presentation of dynamic time-activity data for a PD subject following bolus injection of $^{123}$I Altropane and imaged over 60 min.
Figure 2A:
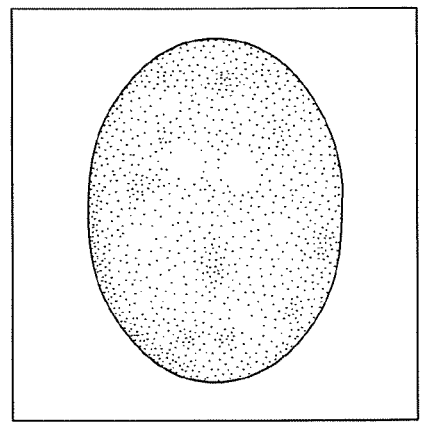
FIG. 2a is an image corresponding to the data of FIG. 2.

Following injection of $^{123}$I Altropane in controls and PD subjects peak striatal count densities are noted at 10 minutes post-injection. (FIGS. 1 and 2). It is noted that most subjects exhibit rapid elimination of Altropane from brain. FIG. 1. is a graphic presentation of dynamic time-activity data for a healthy control subject receiving a bolus injection of $^{123}$I Altropane and imaged over 60 minutes. Peak uptake for striatum occurs by 10 minutes while background uptake peaks on the first acquisition. Both striatal and occipital background regions demonstrate rapid washout. FIG. 1a is an image showing characteristic striatal uptake and homogeneous cortical background. FIG. 2. is a graphic presentation of dynamic time-activity data for a PD subject following bolus injection of $^{123}$I Altropane and imaged over 60 minutes. Peak uptake for striatum and background uptake occurs on the first acquisition. FIG. 2a demonstrates reduced striatal uptake most prominent in the putamen consistent with the known pattern of dopamine transporter loss in PD and visually distinct from the control subject in FIGS. 1 and 1a.

Localization of uptake in striatal structures was well demonstrated in all subjects in the study with the characteristic "comma" shaped appearance of striatal uptake in controls and more asymmetric uptake (left-right asymmetry and caudate>putamen asymmetry) in PD subjects consistent with other dopamine transporter studies using Altropane and other SPECT studies in PD. By 20-30 minutes post injection of $^{123}$I Altropane rates of washout from striatum and occipital background region were similar resulting in stability of the striatal binding ratio.

Binding ratios decrease slightly when moving from 3 imaging heads of projection data to 2 imaging heads of projection data and further when using just one imaging head in the SPECT reconstruction. There is no effect on the shape of the SBR curves, with peak SBRs occurring from 15 minutes post injection for both the one and two head scenarios, suggesting an optimal scanning protocol from the perspective of signal to noise at the points with the highest binding ratios. Table 3 indicates the peak SBRs for PD and control subjects (based on a single scan) demonstrating the small reductions in peak SBR when fewer imaging heads are incorporated into the reconstruction.

Figure 5:
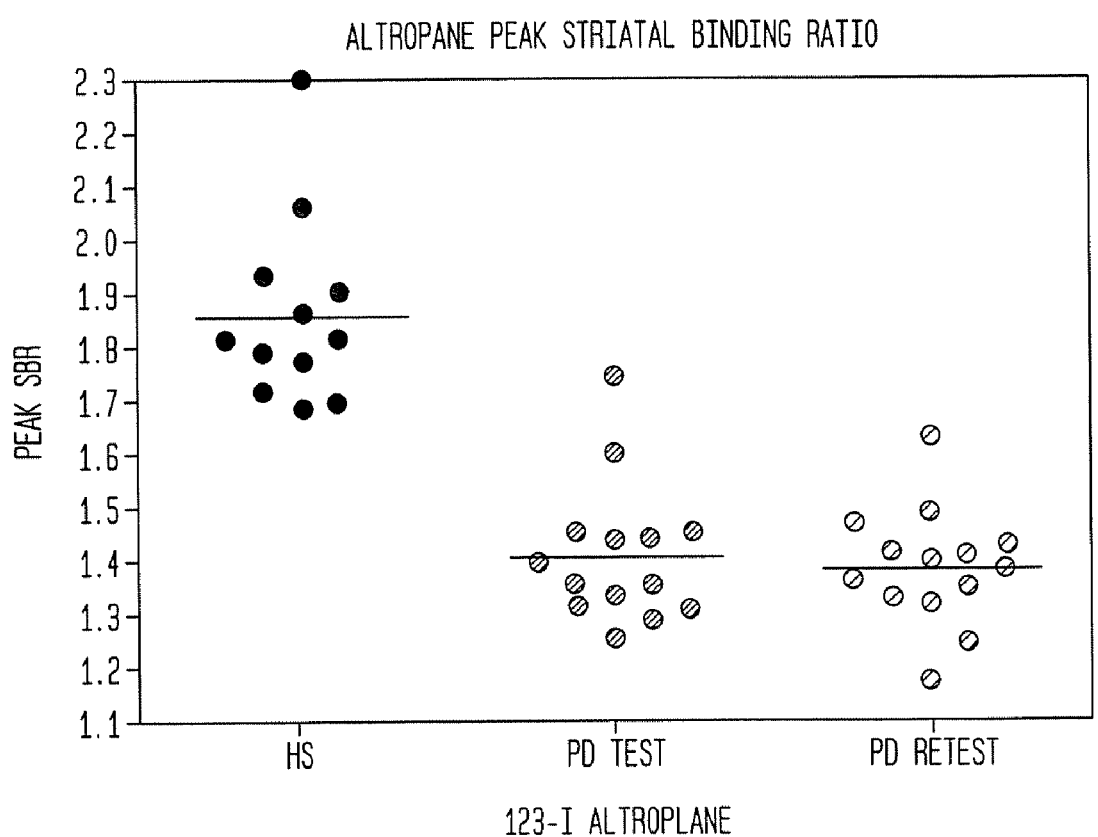
FIG. 5 is a graphic presentation of peak striatal binding ratios (SBR) for PD first and second (retest) study and control subjects.
Figure 6:
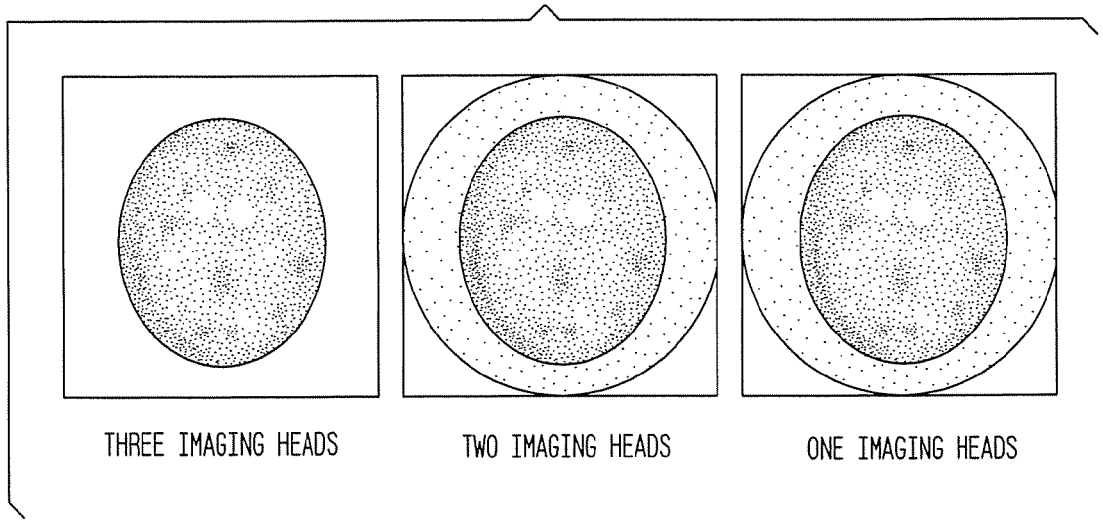
FIG. 6 is a graphic presentation of transaxial SPECT images in a PD subject using three, two and one imaging head(s) for reconstruction.

Examination of the semi-quantitative peak SBR demonstrates differences between the PD and healthy controls (FIGS. 4, 5). FIG. 4. is a graphic presentation of Peak striatal binding ratios (SBR) for PD and control subjects versus age. The SBR is determined as the single scan post injection demonstrating highest uptake. The measure provides excellent separation between this group of well-characterized PD subjects and healthy controls. FIG. 5 is a graphic presentation of peak striatal binding ratios (SBR) for PD first and second (retest) study and control subjects. FIG. 6 is a graphic presentation of transaxial SPECT images in a PD subject using three, two and one imaging head(s) for reconstruction. FIG. 6 depicts images in a PD subject for one, two, and three imaging heads of data processed as a summed image for scans. There is deterioration in the visual quality of these images for data acquired from a single head after 8 mCi $^{123}$I Altropane injection.

Test-Retest Reproducibility of $^{123}$I Altropane Injection in PD

The test-retest reproducibility of the SPECT imaging was assessed in all 15 PD subjects using a mean total binding ratio taken as the mean of scan number 3 through six corresponding to roughly 30 minutes of imaging commencing about 15 min after bolus injection of $^{123}$I Altropane. For this measure the percent test/retest reproducibility is defined as: (ratio test−ratio retest)/(ratio test) expressed as a percent. The results for all PD subjects under conditions of 3, 2, and 1 imaging head data reconstructions are described in Table 4.

TABLE 4

Total striatal binding ratios

| Subject No. | 3 heads Ratio (3-6) | 2 heads Ratio (3-6) | 1 head Ratio (3-6) |
|---|---|---|---|
| 1 | 1.30 | 1.27 | 1.25 |
| 2 | 1.37 | 1.32 | 1.26 |
| % test/retest | 5.2 | 3.7 | 1.1 |
| 3 | 1.27 | 1.24 | 1.20 |
| 4 | 1.32 | 1.29 | 1.29 |
| % test/retest | 3.5 | 4.2 | 7.7 |
| 5 | 1.30 | 1.27 | 1.23 |
| 6 | 1.39 | 1.35 | 1.29 |
| % test/retest | 6.3 | 6.4 | 4.8 |
| 7 | 1.41 | 1.37 | 1.30 |
| 8 | 1.33 | 1.31 | 1.26 |
| % test/retest | 6.1 | 4.8 | 3.2 |

TABLE 4-continued

| | Total striatal binding ratios | | |
|---|---|---|---|
| Subject No. | 3 heads Ratio (3-6) | 2 heads Ratio (3-6) | 1 head Ratio (3-6) |
| 9 | 1.36 | 1.32 | 1.25 |
| 10 | 1.35 | 1.30 | 1.22 |
| % test/retest | 1.1 | 1.5 | 2.9 |
| 11 | 1.38 | 1.36 | 1.29 |
| 12 | 1.45 | 1.43 | 1.37 |
| % test/retest | 4.8 | 4.9 | 6.1 |
| 13 | 1.56 | 1.47 | 1.40 |
| 14 | 1.70 | 1.60 | 1.48 |
| % test/retest | 8.8 | 8.5 | 5.5 |
| 15 | 1.37 | 1.32 | 1.29 |
| 16 | 1.28 | 1.25 | 1.22 |
| % test/retest | 6.3 | 5.2 | 5.8 |
| 17 | 1.23 | 1.21 | 1.20 |
| 18 | 1.20 | 1.19 | 1.16 |
| % test/retest | 2.4 | 2.3 | 3.1 |
| 19 | 1.42 | 1.38 | 1.32 |
| 20 | 1.44 | 1.40 | 1.35 |
| % test/retest | 1.6 | 1.8 | 1.9 |
| 21 | 1.26 | 1.24 | 1.21 |
| 22 | 1.15 | 1.12 | 1.12 |
| % test/retest | 8.3 | 9.9 | 7.5 |
| 23 | 1.29 | 1.26 | 1.21 |
| 24 | 1.31 | 1.27 | 1.25 |
| % test/retest | 1.4 | 1.1 | 3.7 |
| 25 | 1.35 | 1.33 | 1.28 |
| 26 | 1.22 | 1.20 | 1.17 |
| % test/retest | 9.7 | 9.6 | 8.7 |
| 27 | 1.36 | 1.32 | 1.24 |
| 28 | 1.42 | 1.38 | 1.30 |
| % test/retest | 4.7 | 4.7 | 4.3 |
| 29 | 1.50 | 1.45 | 1.37 |
| 30 | 1.40 | 1.33 | 1.26 |
| % test/retest | 6.9 | 8.1 | 7.6 |
| Mean % test/retest difference | 5.14% | 5.11% | 4.94% |

Total striatal binding obtained during the time points corresponding to roughly a 30utes min commencing 15 minutes after 123I Altropane injection demonstrates robust reproducibility in the 15 PD subjects studied. The reduction of counts involved in the reconstruction had no significant impact on the reproducibility measure used in this analysis.

Procedural Efficiency Recommends the Following
 a) Single rapid or bolus injection of 8 mCi of $^{123}$I Altropane administered after the subject is positioned on the imaging table,
 b) Initiate a single 30 minutes SPECT acquisition commencing at 15 minutes after administration of $^{123}$I Altropane,
 c) Scans are performed on dual and triple-headed SPECT tomographs.

In alternative embodiments, $^{123}$I Altropane is administered at various low and high dose ranges or in single headed camera settings by utilizing various reconstruction and filtration strategies. For example, employing an iterative reconstruction of these data would improve the signal to noise properties of the image. In one embodiment, one or more filters are used on the 2D or 3D data sets.

The findings from this dataset are generalizable. In one embodiment, reconstruction and filtration of the $^{123}$I Altropane imaging data uses commonly available and standard algorithms that might be encountered in a typical clinical nuclear medicine setting.

INCORPORATION BY REFERENCE

The patent and scientific literature referred to herein establishes knowledge that is available to those of skill in the art. All issued patents, patent applications, published foreign applications, and published references, which are cited herein, are hereby incorporated by reference to the same extent as if each was specifically and individually indicated to be incorporated by reference in their entirety.

EQUIVALENTS

Those skilled in the art will recognize, or be able to ascertain, using no more than routine experimentation, numerous equivalents to the specific embodiments described specifically herein. Such equivalents are intended to be encompassed in the scope of the Claims.

REFERENCES

Seibyl J, Marek K, Sheff K, et al. Iodine-123-beta-CIT and Iodine-123-FPCIT SPECT Measurement of Dopamine Transporters in Healthy Subjects and Parkinson's Patients. *J. Nucl. Med.* 39:1500-07, 1998.

Marek K, Seibyl J: Tech/Sight Imaging: A molecular map for neurodegeneration. *Science* 289(5478): 409-11, 2000.

Seibyl J, Marek K, Quinlan D, Sheff K, Zoghbi S, Zea-Ponce Y, Baldwin R, Fussell B, Smith E, Charney D, Hoffer P, Innis R. Decreased SPECT [123-I]β-CIT striatal uptake correlates with symptom severity in idiopathic Parkinson's disease. *Annals of Neurology*, 38:589-98, 1995.

Seibyl J, Marek K, Sheff K, Baldwin R, Zoghbi S, Zea-Ponce Y, Charney D, van Dyck C, Hoffer P, Innis R. Test/retest reproducibility of [123I]β-CIT SPECT brain measurement of dopamine transporters in Parkinson's patients. *J. Nucl. Med.* 38:1453-59, 1997.

Laruelle M, Wallace E, Seibyl J, Baldwin R, Zea-Ponce Y, Zoghbi S, Neumeyer J, Charney D S, Hoffer P B, Innis R B. Graphical, kinetic, and equilibrium analyses of in vivo [123I]β-CIT binding to dopamine transporters in healthy human subjects. *J. Cereb. Blood Flow Metab.* 14:982-94, 1994.

Kugaya, A., Seneca, N. M. Snyder, P. J., Williams, S. A., Malison, R. T., Baldwin, R. M., Seibyl, J. P., Innis, R. B., Changes in human in vivo serotonin and dopamine transporter availabilities during chronic antidepressant administration. *Neuropsychopharmacology*, 28(2):413-20, 2003.

Sahani, D., S. Saini, G. A. Fatuga, E. F. Halpern, M. E. Lanser, J. B. Zimmerman, and A. J. Fischman, *Quantitative measurements of medical images for pharmaceutical clinical trials: comparison between on-site and off-site assessments*. AJR Am J Roentgenol, 2000. 174(4): p. 1159-62.

Fischman, A. J., A. A. Bonab, J. W. Babich, E. P. Palmer, N. M. Alpert, D. R. Elmaleh, R. J. Callahan, S. A. Barrow, W. Graham, P. C. Meltzer, R. N. Hanson, and B. K. Madras, *Rapid detection of Parkinson's disease by SPECT with altropane: a selective ligand for dopamine transporters*. Synapse, 1998. 29(2): p. 128-41.

Madras, B. K., L. M. Gracz, M. A. Fahey, D. Elmaleh, P. C. Meltzer, A. Y. Liang, E. G. Stopa, J. Babich, and A. J. Fischman, *Altropane, a SPECT or PET imaging probe for dopamine neurons: III. Human dopamine transporter in postmortem normal and Parkinson's diseased brain*. Synapse, 1998. 29(2): p. 116-27.

Madras, B. K., L. M. Gracz, P. C. Meltzer, A. Y. Liang, D. R. Elmaleh, M. J. Kaufman, and A. J. Fischman, *Altropane, a SPECT or PET imaging probe for dopamine neurons: II. Distribution to dopamine-rich regions of primate brain*. Synapse, 1998. 29(2): p. 105-15.

Madras, B. K., P. C. Meltzer, A. Y. Liang, D. R. Elmaleh, J. Babich, and A. J. Fischman, *Altropane, a SPECT or PET*

*imaging probe for dopamine neurons: I. Dopamine transporter binding in primate brain.* Synapse, 1998. 29(2): p. 93-104.

Fischman, A. J., J. W. Babich, D. R. Elmaleh, S. A. Barrow, P. Meltzer, R. N. Hanson, and B. K. Madras, *SPECT imaging of dopamine transporter sites in normal and MPTP-Treated rhesus monkeys.* J Nucl Med, 1997. 38(1): p. 144-50.

What is claimed is:

1. A method for assessing dopamine transporter levels in a selected area of a subject's central nervous system by SPECT imaging comprising the steps of:
    a) Administering to the subject a labeled dopamine transporter ligand at approximately the time the subject is positioned for SPECT imaging;
    b) Initiating at least one SPECT acquisition of said selected area for a duration of about 30 minutes commencing at about 15 minutes after administration of the labeled dopamine transporter ligand; and
    c) Assessing, at least in part based on said SPECT acquisition, the amount of said labeled dopamine transporter ligand that is bound to dopamine transporter in said selected area.

2. The method of claim 1, wherein the labeled dopamine transporter ligand is $^{123}$I Altropane.

3. The method of claim 1, wherein the labeled dopamine transporter ligand is administered at a dose of about 8 mCi.

4. The method of claim 1, wherein said selected area comprises a portion of the brain.

5. The method of claim 3, wherein said portion of the brain comprises the striatum.

6. A method for assessing the disposition of Altropane in a subject by SPECT imaging comprising the steps of:
    a) Administering to the subject a labeled dopamine transporter ligand at approximately the time the subject is positioned for SPECT imaging;
    b) Initiating at least one SPECT acquisition of a selected area for a duration of about 30 minutes commencing at about 15 minutes after administration of the labeled dopamine transporter ligand; and
    c) Assessing, at least in part based on said SPECT acquisition, the amount of labeled dopamine transporter ligand that is bound to dopamine transporter in said selected area.

7. A method for assessing dopamine transporter levels in a selected area of a subject's central nervous system by SPECT imaging comprising the steps of:
    a) Administering to the subject a labeled dopamine transporter ligand at approximately the time the subject is positioned for SPECT imaging;
    b) Initiating at least one SPECT acquisition of said selected area for an imaging effective duration wherein said duration fails within a secular equilibrium commencing period, said duration is about 30 minutes commencing about 15 minutes after administration of the labeled dopamine transporter ligand; and
    c) Assessing, at least in part based on said SPECT acquisition, the amount of said labeled dopamine transporter ligand that is bound to dopamine transporter in said selected area.

8. The method of claim 4, wherein said labeled dopamine transporter ligand is $^{123}$I Altropane.

9. The method of claim 5, wherein said labeled dopamine transporter ligand is administered at a dose of about 8 mCi.

10. The method of claim 5, wherein said selected area comprises a portion of the brain.

11. The method of claim 7, wherein said portion of the brain comprises the striatum.

12. A method for assessing dopamine transporter levels in a selected area of a subject's central nervous system by SPECT imaging comprising the steps of:
    a) Administering to the subject a labeled dopamine transporter ligand at approximately the time the subject is positioned for SPECT imaging;
    b) Initiating at least one SPECT acquisition of said selected area for a duration of about 30 minutes commencing at secular equilibrium wherein said secular equilibrium is about 15 minutes after administration of the labeled dopamine transporter ligand; and
    c) Assessing, at least in part based on said SPECT acquisition, the amount of said labeled dopamine transporter ligand that is bound to dopamine transporter in said selected area.

* * * * *